United States Patent [19]

Shikakura et al.

[11] 4,012,449
[45] Mar. 15, 1977

[54] PRODUCTION OF METHACROLEIN AND OXIDATION CATALYST USED THEREFOR

[75] Inventors: Yoshihisa Shikakura; Fumio Sakai; Hitoshi Shimizu, all of Takasaki, Japan

[73] Assignee: Nippon Kayaku Kabushiki Kaisha, Tokyo, Japan

[22] Filed: Nov. 4, 1975

[21] Appl. No.: 628,658

[30] Foreign Application Priority Data

Nov. 27, 1974 Japan .......................... 49-135569

[52] U.S. Cl. .................... 260/603 R; 260/604 R; 252/432
[51] Int. Cl.² ................. C07C 45/16; B01J 21/02; C07C 45/02
[58] Field of Search ............... 252/432; 260/604 R, 260/603 R

[56] References Cited

UNITED STATES PATENTS

| | | | |
|---|---|---|---|
| 3,446,840 | 4/1969 | Kato | 252/432 |
| 3,642,930 | 2/1972 | Grasselli | 260/680 E |
| 3,778,386 | 12/1973 | Takenaka | 260/604 R |
| 3,803,204 | 4/1974 | Grasselli | 252/432 |

FOREIGN PATENTS OR APPLICATIONS 947,772  5/1974  Canada ............................ 252/432

1,249,290  10/1971  United Kingdom .............. 252/432

*Primary Examiner*—Winston A. Douglas
*Assistant Examiner*—John F. Niebling
*Attorney, Agent, or Firm*—Lane, Aitken, Dunner & Ziems

[57] ABSTRACT

An oxidation catalyst having the general formula:

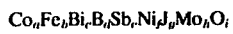

$$Co_aFe_bBi_cB_dSb_eNi_fJ_gMo_hO_i$$

in which J represents at least one of the elements potassium, rubidium, and cesium, and the suffixes $a$, $b$, $c$, $d$, $e$, $f$, $g$, $h$, and $i$ represent the numbers of cobalt, iron, bismuth, boron, antimony, nickel, J, molybdenum, and oxygen atoms, respectively, when $h$ is 12, $a$ is 1 to 15, $b$ 0.3 to 8, $c$ 0.1 to 7, $d$ 0.1 to 3, $e$ 0.01 to 1, $f$ 0 to 5, $g$ 0 to 1 (exclusive of 0), and $i$ is 38 to 92 and is determined by total valences of other elements. There is also provided a process for manufacturing methacrolein by oxidizing isobutylene and/or tertiary butyl alcohol with molecular oxygen, characterized in that the reaction is carried out in the presence of the catalyst as defined above.

7 Claims, No Drawings

PRODUCTION OF METHACROLEIN AND OXIDATION CATALYST USED THEREFOR

BACKGROUND OF THE INVENTION

For the production of methacrolein by the vapor phase oxidation of isobutylene various oxidation catalysts have been proposed.

Japanese patent Publn. Nos. 8992/1969 and 25046/1969, for example, disclose the tellurium oxide-molybdenum oxide catalysts. Catalysts containing tellurium, however, are highly toxic and have a short service life due to the dissipation of tellurium so that these catalysts are not suitable for industrial use. Japanese patent Pbuln. No. 32043/1972 and Laid-open Publn. No. 5710/1973 disclose catalysts containing thallium oxides. Thallium oxides tend to be easily reduced in a reducing atmosphere to oxides of lower valence thallium or metallic thallium, both of which are volatile. Furthermore, thallium is poisonous to humans.

SUMMARY OF THE INVENTION

Therefore, it is an object of this invention to provide a novel catalyst without any of the above-mentioned drawbacks.

Another object of this invention is to provide a novel catalyst suitable for the production of methacrolein from isobutylene and/or tertiary butyl alcohol.

A further object of this invention is to oxidize isobutylene and/or tertiary butyl alcohol with oxygen in the presence of the novel catalyst so as to produce methacrolein.

It has now been discovered these objectives can be obtained with a catalyst having the following formula:

$$Co_a Fe_b Bi_c B_d Sb_e Ni_f J_g Mo_h O_i$$

in which J represents at least one of the elements potassium, rubidium, and cesium, and the suffixes $a$, $b$, $c$, $d$, $e$, $f$, $g$, $h$ and $i$ represent the numbers of cobalt, iron, bismuth, boron, antimony, nickel, J, molybdenum, and oxygen atoms, respectively, when $h$ is 12, $a$ is 1 to 15, $b$ 0.3 to 8, $c$ 0.1 to 7, $d$ 0.1 to 3, $e$ 0.01 to 1, $f$ 0 to 5, $g$ 0 to 1 (exclusive of 0), and $i$ is 38 to 92 determined by total valences of other elements. There is also provided a process for manufacturing methacrolein by oxidizing isobutylene and/or tertiary butyl alcohol with molecular oxygen.

According to this invention methacrolein can be produced from isobutylene and/or tertiary butyl alcohol (hereinafter referred to as "TBA") in a high yield. When the reaction is carried out at a high space velocity methacrolein is available in a reasonable yield. The catalyst according to the invention has a long service life and is nontoxic, which permits it to be applied in industrial use.

An excellent catalyst may be obtained when, in the above formula, $h$ is 12, $a$ 3 to 12, $b$ 0.5 to 5, $c$ 0.5 to 4, $d$ 0.5 to 3, $e$ 0.05 to 1, $f$ 0 to 3, $g$ 0.01 to 0.5, and $i$ 42 to 77.

The catalyst of this invention can be prepared in the conventional manner known in the art, for example, by mixing compounds of essential elements together in the presence of water, drying and then calcining the resulting mass at a temperature of 400° to 750° C and preferably 500° to 700° C, the resulting product being ready for use as the oxidation catalyst.

Various compounds of the essential elements can be used in the preparation of the catalyst. Typical examples are listed below.

Examples of cobalt compounds are cobalt nitrates, cobalt carbonates, cobalt oxalates, and others.

Examples of iron compounds are iron nitrates, iron carbonates, iron oxalates, and others.

Examples of nickel compounds are nickel nitrate, nickel carbonate, nickel oxalate, and others.

Examples of bismuth compounds are bismuth nitrate and others.

Examples of boron compounds are boric acid and others.

Examples of potassium, rubidium, and cesium compounds are nitrates, carbonates, hydroxides and others of the respective elements.

Examples of antimony compounds are antimony trioxide, antimony pentoxide, and others.

Examples of molybdenum compounds are ammonium molybdate, molybdic acid, molybdenum trioxide, and others.

While high yields are obtained even when the catalyst is used without any carrier, the catalyst may be supported on any desirable carrier in suitable amounts.

Examples of carriers which can be used include silica gel, silica sol, diatomaceous earth, alumina, carborundum, and others.

The catalyst of this invention may be used in a fixed bed, fluidized bed or moving bed.

A typical source of the molecular oxygen is generally air. Pure oxygen may also be used alone or together with an inert gas such as nitrogen, carbon dioxide and others as a diluent.

The reactant, isobutylene and/or TBA, is in a gaseous state. It is desirable to add steam to the feed mixture.

The feed mixture introduced into the reaction zone thus consists of isobutylene and/or TBA, molecular oxygen, and steam. The relative proportions of the reactants are not critical to obtaining reaction; however, and preferred molar ratio of isobutylene and/or TBA : oxygen : steam in the mixture is 1 : (0.5–8) : (1–20), particularly 1 : (1.5–5) : (2–8).

When a mixture of isobutylene and TBA is used as the reactant isobutylene and TBA can be mixed in any desirable ratio with excellent results.

The gaseous feed mixture can be introduced at any desirable space velocity, preferably at a space velocity of 360 to 36,000 l-gas/l-cat.hr, especially 720 to 10,800 l-gas/l-cat.hr.

The temperature for carrying out the reaction is not critical. The reaction may preferably be carried out at a temperature of 250° to 500° C, especially 270° to 450° C.

The reaction can be carried out at atmospheric pressure or at lower or higher pressures. In general it is convenient to carry out the reaction at atmospheric pressure. A preferred pressure range is 0.5 to 10 atm.

The following examples are illustrative of the catalyst and the process of this invention. In the examples the terms "reaction rate", "selectivity", "per-pass yield", and "space velocity" are defined as follows.

$$\text{reaction rate (\%)} = \frac{\text{number of moles of reacted isobutylene and/or TBA in feed}}{\text{number of moles of isobutylene and/or TBA in feed}} \times 100$$

$$\text{selectivity (\%)} = \frac{\text{number of moles of methacrolein produced}}{\text{number of moles of reacted isobutylene and/or TBA}} \times 100$$

$$\text{per-pass yield (\%)} = \frac{\text{number of moles of methacrolein produced}}{\text{number of moles of isobutylene and/or TBA}} \times 100$$

$$\text{space velocity} = \frac{\text{flow rate* of a gaseous feed mixture (l-gas/hr)}}{\text{volume of catalyst charge (l-cat.)}}$$

*calculated on the basis of normal temperature and pressure

EXAMPLE 1

In distilled water 42.4 g of ammonium paramolybdate was dissolved and then 0.28 g of potassium nitrate was added thereto. To this solution were added with stirring an aqueous solution containing 40.8 g of cobalt nitrate, an aqueous solution containing 24.2 g of iron nitrate, a dilute nitric acid solution containing 9.7 g of bismuth nitrate, an aqueous solution containing 2.48 g of boric acid, an aqueous solution containing 5.8 g of nickel nitrate and 0.58 g of antimony trioxide. To the resulting slurry-like suspension was further added 19.6 g of silica gel with stirring. This suspension was then evaporated to dryness. The crude product was molded and then calcined at a temperature of 650° C for six hours. This product (Catalyst A) had the following composition.

$$Co_7Fe_3Bi_1B_2Ni_1Sb_{0.1}K_{0.14}Mo_{12}O_{56.7}$$

A reaction tube with an inner diameter of 21 mm was charged with 40 ml of Catalyst A. To this reaction tube a gaseous mixture consisting of 1 mole of isobutylene, 12.4 moles of air, and 8 moles of steam was fed at a space velocity of 1500 l-gas/l-cat.hr. and the reaction temperature was maintained at 350° C. The reaction rate of isobutylene was 98.5%, the selectivity for methacrolein 82.6%, the per-pass yield of methacrolein 81.4%, and the per-pass yield of methacrylic acid 1.2%. Consequently, a total yield of useful products given as a sum of the per-pass yields of methacrolein and methacrylic acid reached 82.6%.

After the reaction had been continuously carried out over a period of 300 hours no deterioration of the catalyst was found.

EXAMPLE 2

The procedures of Example 1 were repeated except that 0.41 g of rubidium nitrate was used instead of 0.28 g of potassium nitrate. The resulting product (Catalyst B) had the following composition.

$$Co_7Fe_3Bi_1B_2Ni_1Sb_{0.1}Rb_{0.14}Mo_{12}O_{56.7}$$

The oxidation reaction was carried out using Catalyst B in the same manner as described in Example 1. The results are shown in Table 2.

EXAMPLE 3

The procedures of Example 1 were repeated except that 0.54 g of cesium nitrate was used instead of 0.28 g of potassium nitrate. The resulting product (Catalyst C) had the following composition.

$$Co_7Fe_3Bi_1B_2Ni_1Sb_{0.1}Cs_{0.14}Mo_{12}O_{56.7}$$

The oxidation reaction was carried out using Catalyst C in the same manner as described in Example 1. The results are shown in Table 2.

EXAMPLES 4–16

By following the procedure as described in Examples 1–3 there were obtained a number of catalysts having the composition shown in Table 1. Each catalyst was used for the oxidation of isobutylene in the same manner as described in Example 1. The results are shown in Table 2.

Table 1

| Example | Co (a) | Fe (b) | Bi (c) | B (d) | Sb (e) | Ni (f) | K | Rb (g) | Cs | Mo (h) | O (i) | | |
|---|---|---|---|---|---|---|---|---|---|---|---|---|---|
| 4 | 7 | 3 | 1 | 2 | 0.1 | — | — | 0.14 | — | 12 | 55.7 | Catalyst | D |
| 5 | 7 | 4 | 1 | 1 | 0.1 | 1 | 0.07 | — | — | 12 | 56.7 | Catalyst | E |
| 6 | 10 | 2 | 0.5 | 1 | 0.1 | — | 0.07 | — | — | 12 | 56.4 | Catalyst | F |
| 7 | 4.5 | 4.5 | 2 | 0.5 | 0.2 | 0.5 | 0.07 | — | — | 12 | 54.1 | Catalyst | G |
| 8 | 8 | 2 | 1.5 | 1 | 0.7 | 1 | 0.07 | — | — | 12 | 56.8 | Catalyst | H |
| 9 | 7 | 1 | 2 | 1 | 0.1 | 2 | — | 0.07 | — | 12 | 56.2 | Catalyst | I |
| 10 | 4 | 0.5 | 4 | 2 | 0.1 | 1 | — | 0.12 | — | 12 | 52.9 | Catalyst | J |
| 11 | 6 | 3 | 1 | 1 | 0.06 | 1 | 0.07 | — | — | 12 | 53.6 | Catalyst | K |
| 12 | 4 | 2 | 1 | 1 | 0.2 | 3 | 0.07 | — | — | 12 | 51.3 | Catalyst | L |
| 13 | 5 | 1 | 1 | 1 | 0.1 | 1 | — | 0.04 | — | 12 | 49.2 | Catalyst | M |
| 14 | 6 | 2 | 1 | 1 | 0.1 | 1 | — | 0.4 | — | 12 | 52.4 | Catalyst | N |
| 15 | 7 | 3 | 1 | 2 | 0.1 | 1 | 0.07 | 0.07 | — | 12 | 56.7 | Catalyst | O |
| 16 | 7 | 3 | 1 | 2 | 0.1 | — | — | — | 0.14 | 12 | 55.7 | Catalyst | P |

Table 2

Production of Metacrolein from Isobutylene

| Example | Catalyst | Reaction Temperature (° C) | Reaction Rate of Isobutylene (%) | Selectivity of Methacrolein (%) | Per-pass Yield of Methacrolein (%) | Per-pass Yield of Methacrylic Acid (%) | Total Yield of Useful Products (%) |
|---|---|---|---|---|---|---|---|
| 2 | B | 355 | 98.3 | 83.6 | 82.2 | 1.6 | 83.8 |
| 3 | C | 355 | 97.1 | 83.0 | 80.6 | 1.9 | 82.5 |
| 4 | D | 350 | 98.6 | 79.7 | 78.6 | 0.9 | 79.5 |
| 5 | E | 350 | 99.4 | 77.5 | 77.1 | 1.1 | 78.2 |
| 6 | F | 355 | 98.5 | 78.3 | 77.1 | 1.7 | 78.8 |
| 7 | G | 355 | 98.1 | 80.6 | 79.1 | 1.3 | 80.4 |
| 8 | H | 360 | 99.2 | 79.3 | 78.7 | 0.8 | 79.5 |

Table 2-continued

Production of Metacrolein from Isobutylene

| Example | Catalyst | Reaction Temperature (°C) | Reaction Rate of Isobutylene (%) | Selectivity of Metha- crolein (%) | Per-pass Yield of Metha- crolein (%) | Per-pass Yield of Methacrylic Acid (%) | Total Yield of Useful Products (%) |
|---|---|---|---|---|---|---|---|
| 9  | I | 350 | 97.2 | 84.2 | 81.8 | 1.3 | 83.1 |
| 10 | J | 360 | 95.7 | 83.0 | 79.4 | 1.7 | 81.1 |
| 11 | K | 345 | 97.5 | 80.6 | 78.6 | 1.9 | 80.5 |
| 12 | L | 350 | 97.3 | 81.3 | 79.1 | 1.3 | 80.4 |
| 13 | M | 340 | 96.5 | 81.3 | 78.5 | 1.4 | 79.9 |
| 14 | N | 360 | 95.8 | 82.7 | 79.2 | 1.6 | 80.8 |
| 15 | O | 350 | 98.1 | 83.2 | 81.6 | 1.9 | 83.5 |
| 16 | P | 355 | 98.3 | 79.5 | 78.1 | 1.0 | 79.1 |

EXAMPLES 17–32

Example 1 was repeated except that TBA was used instead of isobutylene.

The reactions were carried out in the presence of the respective Catalysts A–P. The results are shown in Table 3.

COMPARATIVE EXAMPLE

The procedures of Example 2 were repeated except that antimony trioxide was not added. The resulting product (Catalyst B′) had the following composition:

$Co_7Fe_3Bi_1B_2Ni_1Rb_{0.14}Mo_{12}O_{56.5}$

Table 3

Production of Metacrolein from T B A

| Example | Catalyst | Reaction Temperature (°C) | Reaction Rate of TBA (%) | Selectivity of Metha- crolein (%) | Per-Pass Yield of Metha- crolein (%) | Per-pass Yield of Methacrylic Acid (%) | Total Yield of Useful Products (%) |
|---|---|---|---|---|---|---|---|
| 17 | A | 330 | 100 | 85.5 | 85.5 | 0.5 | 86.0 |
| 18 | B | 335 | 100 | 86.5 | 86.5 | 0.2 | 86.7 |
| 19 | C | 335 | 100 | 85.0 | 85.0 | 0.3 | 85.3 |
| 20 | D | 330 | 100 | 82.5 | 82.5 | 0.5 | 83.0 |
| 21 | E | 330 | 100 | 82.3 | 82.3 | 0.6 | 82.9 |
| 22 | F | 335 | 100 | 81.2 | 81.2 | 0.7 | 81.9 |
| 23 | G | 335 | 100 | 83.4 | 83.4 | 0.5 | 83.9 |
| 24 | H | 340 | 100 | 82.8 | 82.8 | 0.6 | 83.4 |
| 25 | I | 330 | 100 | 85.6 | 85.6 | 0.6 | 86.2 |
| 26 | J | 340 | 100 | 83.2 | 83.2 | 0.4 | 83.6 |
| 27 | K | 330 | 100 | 82.5 | 82.5 | 0.7 | 83.2 |
| 28 | L | 325 | 100 | 83.1 | 83.1 | 0.6 | 83.7 |
| 29 | M | 315 | 100 | 82.6 | 82.6 | 0.8 | 83.4 |
| 30 | N | 340 | 100 | 83.3 | 83.3 | 0.6 | 83.9 |
| 31 | O | 325 | 100 | 85.3 | 85.3 | 0.5 | 85.8 |
| 32 | P | 330 | 100 | 82.2 | 82.2 | 0.8 | 83.0 |

EXAMPLE 33

To a reaction tube charged with Catalyst A a gaseous mixture consisting of 0.2 mole of isobutylene, 0.8 mole of TBA, 12.4 moles of air, and 8 moles of steam was fed at a space velocity of 1500 l-gas/l-cat.hr and the reaction temperature was maintained at 340° C.

The total reaction rate of isobutylene and TBA was 99.0%, the selectivity for methacrolein 82.7%, the per-pass yield of methacrolein 81.9%, the per-pass yield of methacrylic acid 1.0%, and the total yield of useful products 82.9%.

EXAMPLE 34

To a reaction tube charged with Catalyst B a gaseous mixture consisting of 0.5 mole of isobutylene, 0.5 mole of TBA, 12.4 moles of air, and 8 moles of steam was fed at a space velocity of 1500 l-gas/l-cat.hr and the reaction temperature was maintained at 345° C. The total reaction rate of isobutylene and TBA was 99.3%, the selectivity for methacrolein 86.2%, the per-pass yield of methacrolein 85.6%, the per-pass yield of methacrylic acid 1.1%, and the total yield of useful products 86.7%.

The oxidation reaction was carried out using Catalyst B′ in manner similar to that described in Example 1. In this Example the reaction temperature was maintained at 360° C. The reaction rate of isobutylene was 97.8%, the selectivity for Methacrolein 77.2%, the per-pass yield of methacrolein 75.5%, the per-pass yield of methacrylic acid 0.7%, and the total yield of useful products 76.2%.

It is to be understood that the above disclosure is by way of specific example and that numerous modifications and variations are available to those of ordinary skill in the art without departing from the true spirit and scope of this invention.

What is claimed is:

1. An oxidation catalyst having the composition:

$Co_aFe_bBi_cB_dSb_eNi_fJ_gMo_hO_i$ in which J represents at least one element selected from the group consisting of potassium, rubidium and cesium, and the subscripts $a$, $b$, $c$, $d$, $e$, $f$, $g$, $h$ and $i$ represent the numbers of cobalt, iron, bismuth, boron, antimony, nickel, J, molybdenum and oxygen atoms, respectively, with the proviso that the elements are present in a ratio so that when $h$ is 12, $a$ is 1 to 15, $b$ 0.3 to 8, $c$ 0.1 to 7, $d$ 0.1 to 3, $e$ 0.01 to 1, $f$ 0 to 5, $g$ greater than 0 but less than or equal to 1, and $i$ is a number of 38 to 92 which number is determined by the total valences of the other elements.

2. The oxidation catalyst of claim 1 wherein the ratio is such that when $h$ is 12, $a$ is 3 to 12, $b$ 0.5 to 5, $c$ 0.5 to 4, $d$ 0.5 to 3, $e$ 0.05 to 1, $f$ 0 to 3, $g$ 0.01 to 0.5, and $i$ 42 to 77.

3. A process for manufacturing methacrolein by oxidizing isobutylene and/or tertiary butyl alcohol with molecular oxygen, characterized in that the reaction is carried out in the presence of a catalyst having the composition:

$$Co_aFe_bBi_cB_dSb_eNi_fJ_gMo_hO_i$$

in which J represents at least one element selected from the group consisting of potassium, rubidium and cesium, and the subscripts $a, b, c, d, e, f, g, h$ and $i$ represent the numbers of cobalt, iron, bismuth, boron, antimony, nickel, J, molybdenum, and oxygen atoms, respectively, with the proviso that the elements are present in a ratio so that when $h$ is 12, $a$ is 1 to 15, $b$ 0.3 to 8, $c$ 0.1 to 7, $d$ 0.1 to 3, $e$ 0.01 to 1, $f$ 0 to 5, $g$ greater than 0 but less than or equal to 1, and $i$ is a number of 38 to 92 which number is determined by the total valances of other elements.

4. The process of claim 3 wherein $h$ is 12, $a$ 3 to 12, $b$ 0.5 to 5, $c$ 0.5 to 4, $d$ 0.5 to 3, $e$ 0.05 to 1, $f$ 0 to 3, $g$ 0.01 to 0.5, and $i$ 42 to 77.

5. The process of claim 3 wherein the reaction is carried out in the presence of steam.

6. The process of claim 3 wherein the reactant is isobutylene.

7. The process of claim 3 wherein the reactant is tertiary butyl alcohol.

* * * * *

Notice of Adverse Decision in Interference

In Interference No. 101,495, involving Patent No. 4,012,449, Y. Shikakura, F. Sakai and H. Shimizu, PRODUCTION OF METHACROLEIN AND OXIDATION CATALYST USED THEREFOR, final judgment adverse to the patentees was rendered July 21, 1986, as to claims 3, 4 & 6.

[*Official Gazette September 16, 1986.*]